United States Patent
Elliott et al.

(10) Patent No.: US 10,869,987 B2
(45) Date of Patent: Dec. 22, 2020

(54) PULSE SATURATION OXYGEN DELIVERY SYSTEM AND METHOD

(71) Applicant: B/E Aerospace, Inc., Wellington, FL (US)

(72) Inventors: Andrew Elliott, Shawnee, KS (US); Mrinal Nagrecha, Wichita, KS (US)

(73) Assignee: B/E AEROSPACE, INC, Winston Salem, NC (US)

( * ) Notice: Subject to any disclaimer, the term of this patent is extended or adjusted under 35 U.S.C. 154(b) by 337 days.

(21) Appl. No.: 14/573,998

(22) Filed: Dec. 17, 2014

(65) Prior Publication Data

US 2015/0174359 A1 Jun. 25, 2015

Related U.S. Application Data

(60) Provisional application No. 61/919,007, filed on Dec. 20, 2013.

(51) Int. Cl.
*A61M 16/10* (2006.01)
*A61M 16/00* (2006.01)
(Continued)

(52) U.S. Cl.
CPC ...... *A61M 16/1005* (2014.02); *A61M 16/024* (2017.08); *A61M 16/125* (2014.02); *A62B 7/14* (2013.01); *A61M 16/101* (2014.02); *A61M 2202/0208* (2013.01); *A61M 2205/502* (2013.01); *A61M 2205/587* (2013.01); *A61M 2230/04* (2013.01); *A61M 2230/205* (2013.01);
(Continued)

(58) Field of Classification Search
CPC .. A62B 7/14; A62B 9/00; A62B 9/006; A62B 18/02; A62B 18/025; A62B 18/08; A62B 25/005; A61M 16/1005; A61M 16/125; A61M 16/024; A61M 2016/1025; A61M 2230/205
See application file for complete search history.

(56) References Cited

U.S. PATENT DOCUMENTS 5,365,922 A * 11/1994 Raemer ............... A61B 5/0833
128/202.22
5,664,566 A 9/1997 McDonald et al.
(Continued)

FOREIGN PATENT DOCUMENTS

CN 103415325 A 11/2013
WO WO 99/04841 A1 2/1999

OTHER PUBLICATIONS

Benaron, David A. et al.; "Continuous, Noninvasive, and Localized Microvascular Tissue Oximetry Using Visible Light Spectroscopy"; Jun. 2004; Anesthesiology; V 100, No. 6; pp. 1469-1475.*
(Continued)

*Primary Examiner* — Valerie L Woodward
(74) *Attorney, Agent, or Firm* — Locke Lord LLP (57) ABSTRACT

A system and method for delivering oxygen to a passenger of an aircraft including a a supply of oxygen, an oral-nasal mask, a controller for adjusting a flow of oxygen from the supply of oxygen to the oral-nasal mask, and a sensor for determining a user's blood oxygen saturation level, wherein the controller adjusts the flow of oxygen based on the sensor's determination of the user's blood oxygen saturation level.

18 Claims, 4 Drawing Sheets

(51) Int. Cl.
*A61M 16/12* (2006.01)
*A62B 7/14* (2006.01)
*A61B 18/02* (2006.01)
*A62B 9/00* (2006.01)
*A62B 18/02* (2006.01)

(52) U.S. Cl.
CPC ........ *A61M 2230/432* (2013.01); *A62B 9/006* (2013.01); *A62B 18/025* (2013.01)

(56) References Cited

U.S. PATENT DOCUMENTS

| | | | |
|---|---|---|---|
| 6,186,142 B1 | 2/2001 | Schmidt et al. | |
| 6,401,714 B1 | 6/2002 | Giorgini | |
| 7,246,620 B2* | 7/2007 | Conroy, Jr. | ........ A61B 5/14551 128/204.29 |
| 7,383,105 B2 | 6/2008 | Conroy | |
| 7,784,463 B2 | 8/2010 | Cannon | |
| 8,028,700 B2 | 10/2011 | Hannah et al. | |
| 8,584,674 B1 | 11/2013 | Poliard | |
| 2001/0039951 A1 | 11/2001 | Strickland, Jr. | |
| 2002/0139368 A1* | 10/2002 | Bachinski | ............. A61M 16/06 128/204.23 |
| 2002/0195105 A1 | 12/2002 | Blue et al. | |
| 2004/0163648 A1 | 8/2004 | Burton | |
| 2004/0206353 A1* | 10/2004 | Conroy, Jr. | ........ A61B 5/14551 128/204.23 |
| 2005/0103342 A1 | 5/2005 | Jorczak et al. | |
| 2006/0011199 A1 | 1/2006 | Rashad et al. | |
| 2006/0213519 A1* | 9/2006 | Schmidt | ................ A61M 16/00 128/204.23 |
| 2008/0000480 A1 | 1/2008 | Cannon | |
| 2009/0301489 A1* | 12/2009 | Bloch | ..................... A62B 7/14 128/204.23 |
| 2010/0192952 A1* | 8/2010 | Melker | ............. A61M 16/0627 128/204.23 |
| 2011/0197891 A1 | 8/2011 | Sanders | |
| 2012/0160244 A1 | 6/2012 | Sharma | |
| 2013/0152933 A1* | 6/2013 | Lischer | ................. A61M 16/12 128/204.23 |
| 2013/0306073 A1* | 11/2013 | Fromage | .................. A62B 7/14 128/204.22 |
| 2015/0174359 A1 | 6/2015 | Elliott et al. | |
| 2015/0320953 A1 | 11/2015 | Acker et al. | |

OTHER PUBLICATIONS

International Search Report, dated Aug. 11, 2015, 6 pages, from PCT/US2014/071178, published as WO 2015/095532 dated Jun. 25, 2015.
Written Opinion dated Aug. 11, 2015 in PCT/US2014/071178.
Office Action dated Jul. 27, 2016 in European Patent Application No. 14825233.1.
Office Action issued in Canadian Patent Application No. 2933599 dated Mar. 5, 2018. 4 pages.
Office Action issued in European Patent Application No. 14825233.1 dated Mar. 28, 2018. 10 pages.
First Office Action on Chinese Application No. 201480069607.3 dated Jul. 11, 2018. 15 pages.
Office Action on Canadian patent application No. 2933599 dated Sep. 25, 2018. 4 pages.
Second Office Action on Chinese Application No. 201480069607.3 dated Feb. 1, 2019. 10 pages.
Third Office Action issued in CN Application No. 2014800696073 dated Jul. 11, 2019. 28 pages.
Decision of Rejection issued in CN Application No. 2014800696073 dated Mar. 4, 2020. 10 pages.

* cited by examiner

PULSE SATURATION OXYGEN DELIVERY SYSTEM AND METHOD

CROSS-REFERENCES TO RELATED APPLICATIONS

This application claims priority from U.S. Application No. 61/919,007, filed Dec. 20, 2013, the contents of which are incorporated by reference in its entirety.

BACKGROUND

The present invention generally relates to emergency oxygen supply systems such as those that are routinely carried on commercial aircraft and that deploy automatically upon loss of cabin pressure. More particularly, the invention pertains to enhancing the efficiency with which the supplied oxygen is used to thereby reduce the total amount of oxygen that needs to be carried on an aircraft.

Emergency oxygen supply systems are commonly installed on aircraft for the purpose of supplying oxygen to passengers upon loss of cabin pressure at altitudes above about 12,000 feet. Emergency systems of this type typically include a face mask adapted to fit over the mouth and nose of the passenger when released from an overhead storage compartment. The face mask is connected to an onboard oxygen reserve that can distribute oxygen under low pressure to the passengers. The supplemental oxygen delivered to the mask increases the passenger's blood oxygen saturation level beyond what would be experienced if ambient air were breathed at the prevailing cabin pressure altitude condition. The flow of oxygen provided by the oxygen reserve is estimated to be sufficient to sustain all passengers until cabin pressure is reestablished or until a lower, safer altitude can be reached.

In some emergency oxygen delivery systems, the face mask has an attached reservoir bag into which a flow of oxygen is directed upon deployment of the system and upon activation of the individual face mask via a pull cord. The oxygen is supplied at a constant rate that is calculated to accommodate a worst case scenario, namely to satisfy the need of a passenger with a significantly larger than average tidal volume who is breathing at a faster than average respiration rate when cabin pressure is lost at maximum cruising altitude. In a typical breathing mask, a total of three valves serve to coordinate flows between the bag and the mask, and between the mask and the surroundings. An inhalation valve serves to confine the oxygen flowing into the bag to the bag while the passenger is exhaling as well as during the post-expiratory pause, while preventing any reverse flow from the mask into the bag. When the passenger inhales, the inhalation valve opens to allow for the inhalation of the oxygen that has accumulated in the bag. Upon depletion of the accumulated oxygen, the dilution valve opens to allow cabin air to be drawn into the mask. The continuing flow of oxygen into the bag and through the open inhalation valve into the mask is thereby diluted by the cabin air that is inhaled during the balance of the inhalation phase. During exhalation, the exhalation valve opens to allow a free flow from the mask into the surroundings while the inhalation valve closes to prevent flow from the mask back into the bag. All three valves remain closed during the post-expiratory pause while oxygen continues to flow into the reservoir bag.

Inefficiencies in an emergency oxygen supply system can require the oxygen storage or oxygen generation means to be larger and therefore weigh more than necessary, which of course has an adverse impact on the payload capacity and fuel consumption of the aircraft. Enhancing the efficiency of such a system either in terms of the generation, storage, distribution or consumption of oxygen could therefore yield a weight savings, particularly when multiplied over hundreds of flights. Conversely, an enhancement of a system's efficiency without a commensurate downsizing would impart a larger margin of safety in the system's operation. It is therefore highly desirable to enhance the efficiency of an emergency oxygen supply system in any way possible.

US Patent Application No. 08/0000480 to Cannon described a system for improving the rate of oxygen consumption on an aircraft emergency oxygen system. The improved efficiency is achieved by a reduction in the rate of oxygen consumption by adjusting the allotment of oxygen to each individual passenger as function of such passenger's actual demand, inducing the passenger to more efficiently use such allotment. More particularly, allotment is adjusted as a function of each passenger's respiration rate wherein faster breathing results in a faster delivery rate of the passenger's oxygen allotments. More efficient use of the delivered oxygen is induced by timing the delivery of oxygen so that it is inhaled into the most absorption efficient region of the lung and by limiting the volume of the delivered oxygen so as to approximately coincide with the volume of that region of the lung. Cabin air is relied upon to fulfill the balance of the passenger's respiratory volume. However, Cannon's system presumes a uniform oxygen effectiveness in the passenger, but different passengers consume oxygen at different efficiencies. The present invention is directed to an improved system that measures the oxygen content in the passenger's system, and adjusts the flow of oxygen into the mask based on the measurement.

SUMMARY OF THE INVENTION

The present invention utilizes a pulse oximeter connected to the passenger/patient and uses the readings as a basis to deliver a dose of oxygen to the user. The pulse oximeter may be based on a number of non-invasive technologies to measure the users oxygen blood saturation levels ($SpO_2$).

The timing of the pulse saturation system is controlled by the existing OCS, but the dosage amount varies depending on the user's particular $SpO_2$, making for a much more efficient delivery system. As an example, one could reduce the oxygen pulse by half, thereby doubling the system usage time, or reduce the size of the storage vessel. In hospitals, medical treatment facilities or in emergency situations, instead of monitoring the blood saturation of the patient and making manual changes to the regulated delivery system, this system can set the oxygen delivery rate based on a specific oxygen saturation level (e.g. 97% $O_2$ saturation) and the system would adjust dosing to the patient automatically, until the saturation level is achieved. At that time, it would progressively move towards a nominal value, but if the patient ever fell below the set point again, the system would detect the saturation deficiency and readjust the pulse amount to get the saturation back to the required set point amount. The system may also have an operating range, e.g., a minimum oxygen dose and a maximum oxygen dose. In this situation, regardless of a person's saturation (i.e. 99.9%) they would still receive the minimum dose; and if a user's saturation was always low the system would have a maximum pulse dosage it would provide. This is a precaution to prevent the system from prematurely running out of oxygen.

This type of system has a wide range of applications. Examples include life support systems for passengers on an aircraft, respiratory patients at a hospital or treatment facility, patients on a civilian or military MEDEVAC aircraft.

Other features and advantages of the present invention will become more apparent from the following detailed description of the preferred embodiments in conjunction with the accompanying drawing, which illustrates by way of example the operation of the invention.

DETAILED DESCRIPTION OF THE PREFERRED EMBODIMENTS

The scope of the invention covers aircraft life support systems and aircraft medical support systems, but also covers traditional medical systems where oxygen is delivered to a patient. For convenience the disclosure below will focus on a passenger oxygen delivery system, but it is understood that the invention is not limited to this purpose and extends to other applications.

The system of the present invention uses the application of a pulse oximeter as a basis to control and adjust a dose of oxygen to the user by real time measurements of the user's blood oxygen levels. The prior art pulse oxygen systems deliver a pulse dosage amount based on the aircraft's altitude, which is stored in a table of values in the software on an integrated circuit. The method of the present invention detects the patient's blood oxygen saturation levels based on one or more non-invasive technologies to determine the user's oxygen levels ($SpO_2$), and adjusts the oxygen flow rate accordingly. Different technologies to detect blood oxygen saturation are discussed below.

A Pulse Oximeter is essentially a sensor which is placed on a thin part of the patient's body, usually a fingertip or earlobe, or in the case of an infant, across a foot. Light of two different wavelengths is passed through the patient to a photodetector. The changing absorbance at each of the wavelengths is measured, allowing determination of the absorbance of the passenger's oxyhemoglobin. Absorption at these wavelengths differs significantly between oxyhemoglobin and its deoxygenated form. From the absorbance readings, the oxy/deoxyhemoglobin ratio can be calculated from the ratio of the absorption of the red and infrared light.

Capnometry is a breathing monitoring procedure that measures carbon dioxide concentrations in expired gases. The device used during this procedure is called capnometer. It also determines the adequacy of ventilation and the breathing rate of the patient. It works by using infrared frequencies and measuring the amount of light that has been absorbed by $CO_2$ molecules during the breathing process.

Oximeter (e.g., T-Stat Oximeter). By reading the oxygen saturation even in the smallest capillaries, a T-Stat Oximeter determines the oxygen levels even in patients with no pulse. The T-Stat Oximeter is a Visible Light Spectroscopy (VLS) system that monitors the blood oxygen levels in microvascular tissues. If a traditional pulse oximeter's readings are indicated as a $SpO_2$ percentage, the new T-Stat Oximeter displays a $StO_2$ percentage. The T-Stat oxygen monitor focuses on the amount of oxygen that reaches small capillaries, even when the blood flow is weak, obstructed, or there is no pulse at all. It is non-invasive, and it operates (as with the pulse oximeter) by interpreting the blood color. However, while a traditional pulse oximeter uses red and infrared light frequencies to measure the ratio of saturated to unsaturated hemoglobin, the T-Stat monitor makes use of shorter wavelengths (green and blue). These light waves can monitor specific tissues (even in the smallest blood vessels—capillaries) and detect the oxygen levels at that location.

The device consists of a main electronic monitor and a sensor probe. The monitor collects the data, analyses it and displays the results. The sensor emits light frequencies that illuminate the specific tissue that needs to be studied. When it is returned to the monitor, the reflected light is analyzed and the $StO_2$ estimated.

Figure 1A:
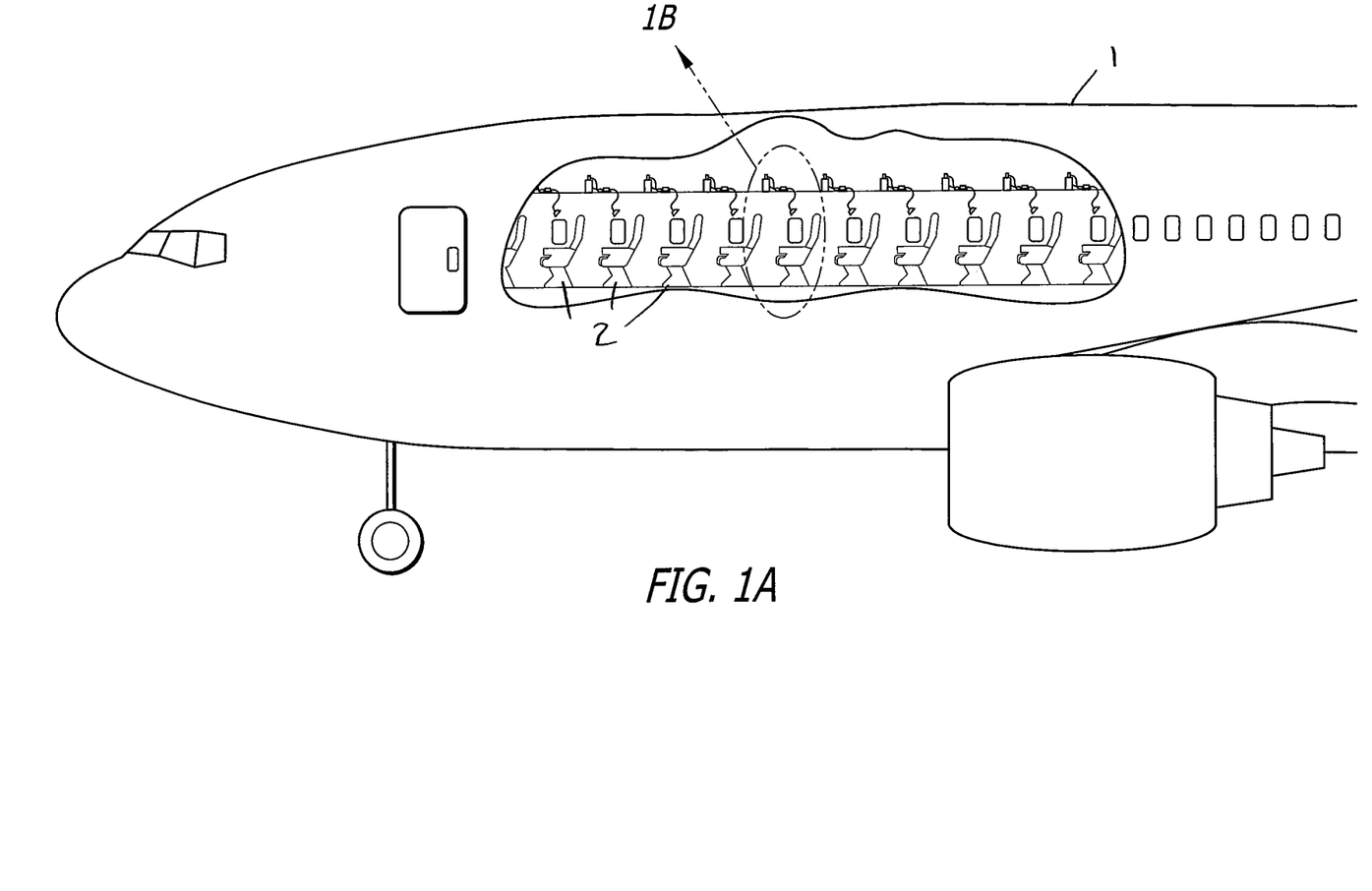
FIG. 1A is an aircraft, partially cut-away, showing a passenger oxygen supply system.
Figure 1B:
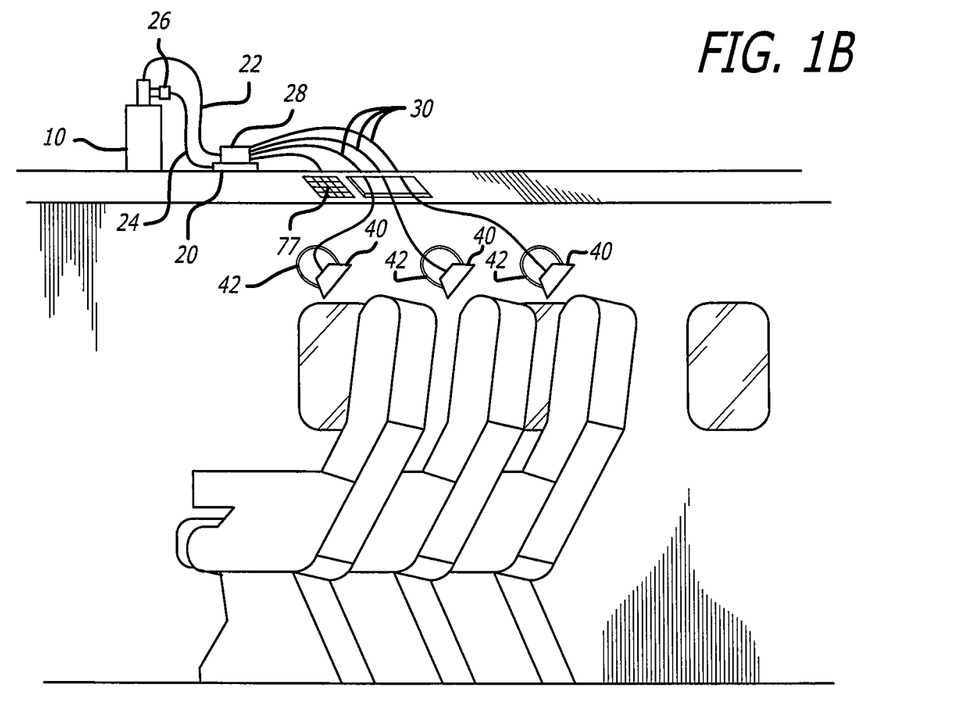
FIG. 1B is an elevated perspective view of an oxygen system of FIG. 1A incorporating a first preferred embodiment of the present invention.

In the present invention, the technologies mentioned above are implemented, individually or in parallel, to provide oxygen saturation data on passengers exposed to a rapid decompression or an environment where oxygen levels are below nominal. FIG. 1A illustrates an aircraft 1 will seats 2 and above the seats are passenger oxygen supply systems. FIG. 1B illustrates the oxygen supply system in more detail, including an oxygen supply tank 10 that is connected to a controller 20 both electrically via cabling 22 and also with a flow tube 24 that couples to a valve 26. The flow tube 24 is connected to a manifold 28 that can adjust the flow of oxygen through the manifold based on commands from the processor. The adaptive controller 20 thus delivers a small dosage of oxygen to a passenger/patient through an elongate tubing 32 to an oral-nasal mask 40 held in place by an adjustable or elastic strap 42. The controller preferably utilizes a non-invasive oximeter sensor 50 in contact with the patient for measuring the blood hemoglobin oxygen saturation in the patient. The data is then recoded via sensors integrated into an oxygen delivery system such as an oxygen mask 40 and/or on the mask strap 42. The sensor 50 on the mask piece 40 may either on the bridge of the nose, supported by a clamp to provide a secure fit, or on the sides of the mask (see FIG. 3) to get a reading from the capillaries on the cheek(s). A sensor 52 on the mask strap 42 acquires a reading off of the back of the neck. Conservative sensors located on the fingertip or on the earlobes may also be compatible with this system.

The oximeter 50 generates a plurality of blood saturation output signals over a given period of time that are sequentially representative of the patient's blood hemoglobin saturation. The controller 20 evaluates a plurality of the oximeter output signals communicated from the sensor 50 along the tubing 42 to the controller 20 and, based on the evaluation, provides a blood saturation signal. A feedback controller responsive to the output signal sets the fractional amount of oxygen passing through the manifold for each oxygen line that is to be delivered to the patient based on the oxygen level readings. The mask 40 preferably incorporates one or more LEDs 55 that indicate the status of the system's operation. For example, if the red LED is illuminated, it indicates that the mask is not functioning; a yellow LED indicates that the mask is functioning, but it's oxygen sensing capabilities are not active. This indication may be due to the fact that the sensors are not correctly getting any information from the passenger, or that the mask is not in use. Finally, a green LED indicates that the mask is being used correctly, and that the oxygen saturation system is functioning correctly. Other arrangements and alarms/displays are also contemplated by the invention.

The invention may take many different forms, depending upon the application and the intended use. For example, an oxygen mask (FIG. 2) using an oximeter may include an oral-nasal mask 40 incorporating an inlet valve 60, outlet valve 62, an inlet 64 for the tubing 32 that supplies oxygen as well as signal or power cabling if present, a controller as part of a Personal Service Unit (PSU) that regulates the supply of oxygen to the aforementioned oral-nasal mask, and oxygen sensing equipment implemented on (but not limited to) the bridge of the nose, secured with a nose-clip, the cheeks, ear-lobes, finger-tips, or the back of the neck. One or more of the following can be used to measure the oxygen levels: (1) a pulse oximeter can be implemented to detect the oxygen saturation of the arterial blood of the passenger; (2) the technique of capnometry can be implemented to detect the percentage of carbon dioxide in the exhaled breath of the passenger to devise the oxygen saturation and breathing rate; and (3) a T-Stat Oximeter. The T-Stat oximeter performs similarly to a regular pulse oximeter, but is much more powerful and can detect saturation from the smallest capillaries in the human body.

One preferred mode of carrying out the invention is using the breathing device inside a pressurized aircraft cabin in order to provide aviation grade oxygen to passengers seated by the utility of a PSU, or a mobile breathing apparatus. In this case, a control device such as a controller board may be located in the PSU that detects the oxyhemoglobin level of the aircraft passenger utilizing one or a plurality of techniques listed above, utilizes the data derived from the passenger, and implements an algorithm or look-up table that adjusts the oxygen output to correspond to a prescribed saturation level, considering a plurality of physiological criteria as well as aircraft altitude and cabin pressure to prescribe a target saturation level. In a preferred embodiment, the system will include checks to detect erroneous signals, and a series of running averages are maintained to combat a loss in the signal or incorrect readings to prevent overdosing.

Figure 2:
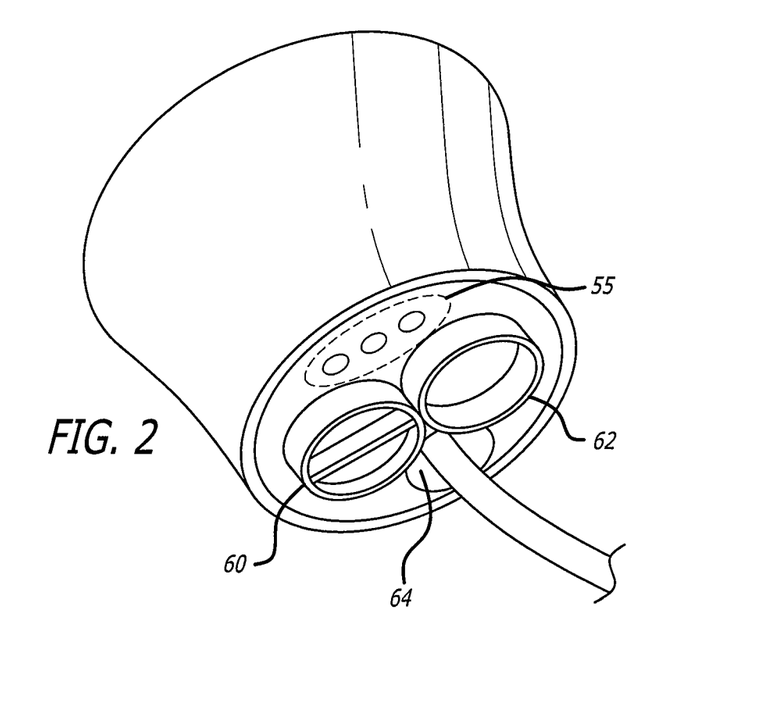
FIG. 2 is an enlarged, elevated perspective view of a front of an oral-nasal mask.

The mask 40 includes an adjustable strap 42 that secures the mask to the passenger, where the mask is typically a frusto-conical thin walled structure providing an airtight seal against the passenger's face. There are three valves on the mask, each operating at a different portion of the breathing cycle. An inhalation valve 60 serves to confine the oxygen flowing into the bag to a bag (not shown) while the passenger is exhaling as well as during the post-expiratory pause and at all times also prevents any flow from the mask into the bag. When the passenger inhales, the inhalation valve 60 opens to allow for the inhalation of the oxygen that has accumulated in the bag. Upon depletion of the accumulated oxygen, the dilution valve 62 opens to allow cabin air to be drawn into the mask 40. The continuing flow of oxygen into the bag and through the open inhalation valve 60 into the mask is thereby diluted by the cabin air that is inhaled during the balance of the inhalation phase. During exhalation, the exhalation valve opens to allow a free flow from the mask into the surroundings while the inhalation valve closes to prevent flow from the mask back into the bag. All three valves remain closed during the post-expiratory pause while oxygen continues to flow into the reservoir bag.

Figure 3:
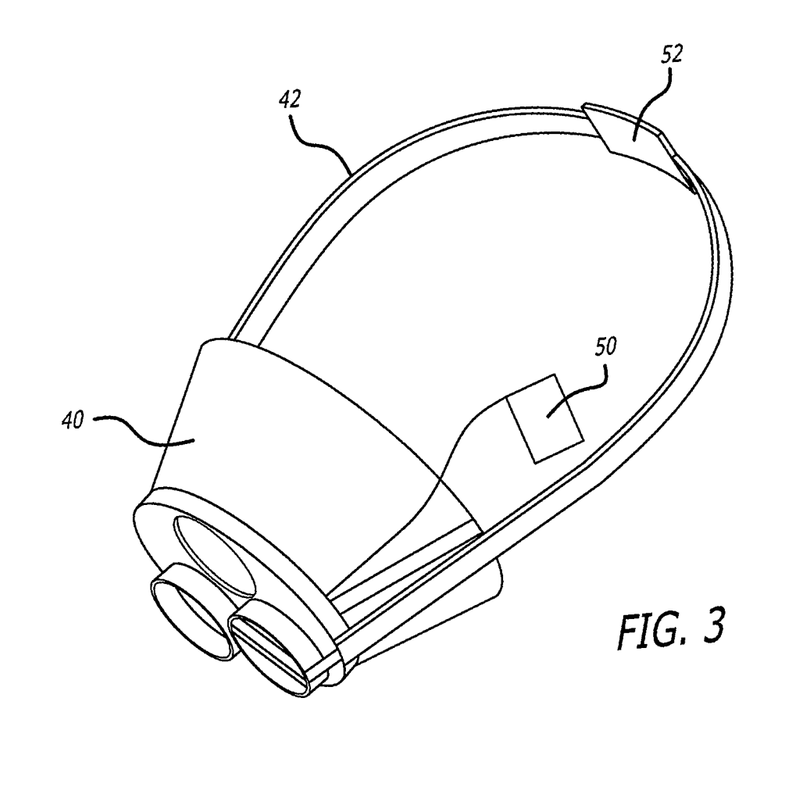
FIG. 3 is an elevated, perspective view of the mask of FIG. 2 on a passenger/patient.

The strap 42 of the mask 40 at the rear portion may include a sensor 52 that comes into contact with the passenger's neck, and can determine an oxygen saturation of the passenger using one of the methods described above. The sensor would be connected to an oxygen flow regulator adjacent the passenger's seat that determined the pulse of oxygen delivered to the passenger. The signal from the sensor could be delivered along the oxygen flow tubing 32 to limit the number of tubes/cables tethered to the mask 40. The sensor could also be located at the wall of the mask, where it could come into contact with the passenger's skin, or worn on a finger or other location.

Figure 4:
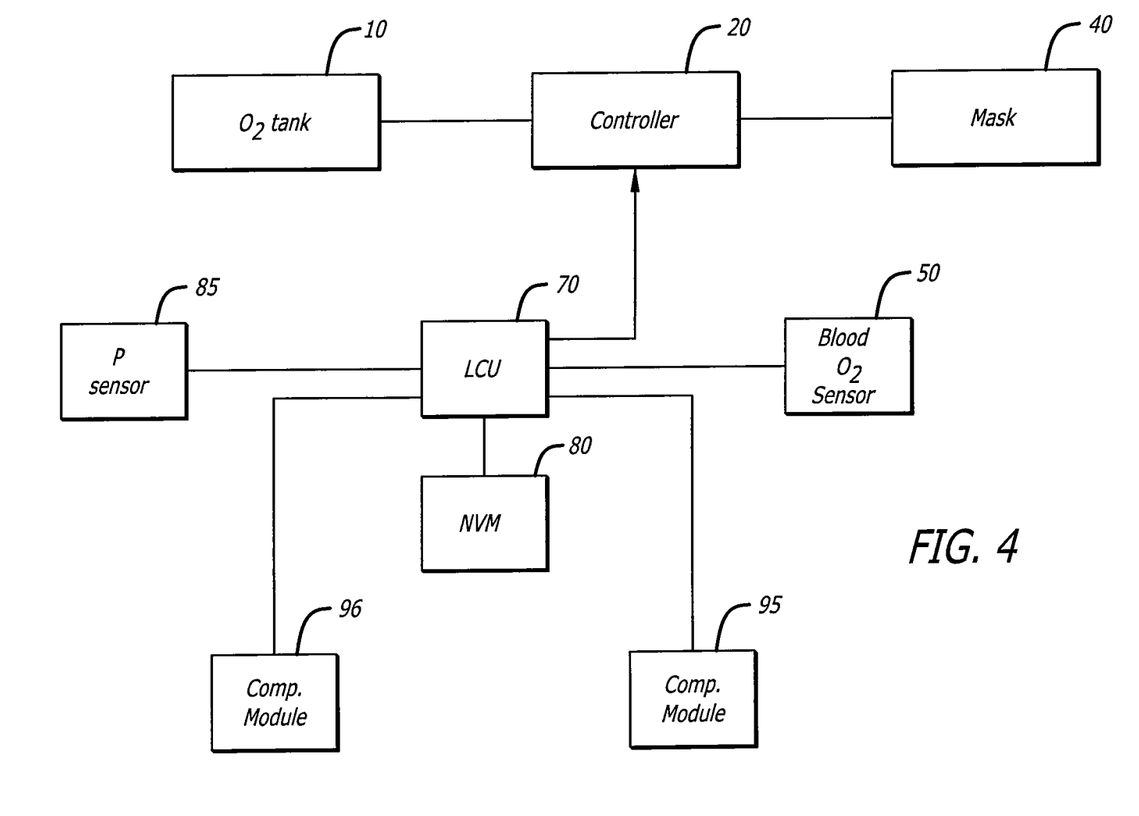
FIG. 4 is a schematic diagram of an alternate embodiment of the present invention.

For continuous-gaseous systems, an active regulation system is preferred that works as a response unit to the controller board that measures and monitors the oxygen saturation level of the passenger's blood. In the case of a pulse demand system, the rate of modulation is dictated by the frequency of inspirations of the individual passenger. Consequently, the pattern of modulation needs to vary accordingly. Utilizing data received from the controller board on the physiological status of the passenger via keyboard 77 or other input device, combined with the state of the aircraft in terms of cabin pressure and altitude, the system regulates an oxygen flow rate and initiates delivery of the oxygen to the passenger.

The invention may further be characterized by an adaptive controller for delivering a small dosage amount of oxygen to a patient, said controller comprising a non-invasive oximeter sensor for measuring blood hemoglobin saturation of the patient, where said oximeter generates a plurality of blood hemoglobin saturation output signal values over a given period of time, sequentially representative of said blood hemoglobin saturation. The controller includes a device for generating and adjusting a running average of said blood hemoglobin saturation output values, and for generating an output signal that is a function of said running average. A processor including checks for identifying possibly invalid output signal values and being responsive to said blood hemoglobin saturation output signal values for evaluating a plurality of said blood hemoglobin saturation output signal values and, based on said evaluation, providing a processed output signal. In the event of error detection, there is preferably means for substituting respective output signals for each of said possibly invalid output signal values thereby forming a sequence of valid output signals.

The adaptive controller may include an oximeter that serves as a pulse oximeter, and said plurality of blood hemoglobin saturation output signal values are oxygen saturation of hemoglobin values as measured by a pulse oximeter ($S_pO_2$). The adaptive controller's processor includes artifact recognition means for identifying possibly invalid output signal values, and for providing a sequence of valid output signal values, exclusive of said identified possibly invalid output signal values; and means for generating a running average of said sequence of valid output signal values and for providing said running average as said processed output signal.

FIG. 4 schematically illustrates a system that may use a non-volatile memory configured for storing a first reference point for start, and increasing a supply of oxygen from an oxygen bottle or tank 10 coupled to the oxygen controller 20 to the breathing apparatus/mask 40 and for stopping a flow of dilution air from the pressurized aircraft cabin to the breathing apparatus at a preconfigured pressure altitude above the first reference point. The system may also include a logical control unit 70 coupled to the non-volatile memory 80 and a pressure sensor 85, and configured for generating a control signal to regulate the supply of oxygen from the oxygen bottle and the flow of dilution air from the pressurized aircraft cabin via the oxygen regulator to the breathing apparatus by processing the first reference point and the pressure data. The non-volatile memory 80 in some applications will be a flash memory. Another options is for a serial port that is coupled to the logical control unit for receiving oxyhemoglobin saturation data forwarded by a pulse oximeter 50 worn by the subject. The logical control 70 unit may comprise a first comparator module 95 for determining the corresponding altitude using the first lookup table and a second comparator module 96 for generating the control signal based on the rotary displacement. It may also incorporate an amplifier for amplifying the control signal.

It will be apparent from the foregoing that while particular forms of the invention have been illustrated and described, various modifications can be made without departing from the spirit and scope of the invention. Accordingly, it is not intended that the invention be limited, except as by the appended claims.

We claim:

1. A method for delivering oxygen to a user, comprising:
   establishing an oxygen reserve and a conduit for communicating oxygen flow to a user using an aircraft passenger breathing mask comprising an oro-nasal mask piece;
   regulating the flow of oxygen to the user via a controller;
   providing the controller with rules by which the flow of oxygen is to be regulated based on the user's blood oxygen saturation levels;
   providing a first sensor device to non-invasively detect the user's blood oxygen saturation level, the first sensor device including a pulse oximeter, a capnometer, and a visible light spectroscopy (VLS) tissue oximeter, the VLS tissue oximeter detecting the user's blood oxygen saturation level in microvascular tissues of the user by using shorter wavelengths than the pulse oximeter, the pulse oximeter of the sensor device coupled to the oro-nasal mask piece to contact a nose of the user;
   detecting a second value of the blood oxygen saturation level of the user using a second sensor device on a mask strap of the aircraft passenger breathing mask to detect the second value from a back of a neck of the user;
   communicating the user's blood oxygen saturation level to the controller;
   adjusting a flow rate of the oxygen to the user based on the user's blood oxygen saturation levels;
   detecting, by the controller, erroneous signals; and
   adjusting the flow rate of the oxygen using a running average of user blood saturation levels in response to detecting erroneous signals.

2. The method for delivering oxygen to a user of claim 1, wherein the controller is part of a passenger safety unit aboard an aircraft.

3. The method for delivering oxygen to a user of claim 2, wherein the method is performed using a pulse oxygen delivery system.

4. The method for delivering oxygen to a user of claim 2, wherein the VLS tissue oximeter of the first sensor device measures the capillaries in the user's cheek.

5. The method for delivering oxygen to a user of claim 2, wherein the controller uses an altitude of the aircraft as part of the rules by which the flow of oxygen is to be regulated.

6. The method for delivering oxygen to a user of claim 2, wherein the controller uses the running average of user blood saturation levels to adjust the flow rate of the oxygen to the user during a loss of signal during oxygen delivery.

7. The method for delivering oxygen to a user of claim 2, wherein the controller receives physiological data from the user, and utilizes the physiological data as well as the oxygen saturation levels of the user in regulating the flow of oxygen to the user.

8. The method for delivering oxygen to a user of claim 2, wherein the oxygen is diluted with aircraft cabin air prior to being breathed by the user.

9. The method of claim 1, wherein the shorter wavelengths used by the VLS tissue oximeter include wavelengths corresponding to green light.

10. A system for delivering oxygen to a passenger of an aircraft, comprising:
    a supply of oxygen;
    an oral-nasal mask;
    a controller for adjusting a flow of oxygen from the supply of oxygen to the oral-nasal mask, the controller configured to detect erroneous signals;
    a first sensor device for determining a user's blood oxygen saturation level, the first sensor device coupled to the oro-nasal mask piece to contact a bridge of a nose of the user, the first sensor device including a pulse oximeter; and
    a second sensor device on a mask strap of the aircraft passenger breathing mask, the second sensor device configured to detect a second value of the blood oxygen saturation level of the user from a back of a neck of the user;
    wherein the controller adjusts the flow of oxygen based on the determination of the user's blood oxygen saturation level by the first sensor device and the second sensor device and using a running average of user blood saturation levels in response to detecting erroneous signals.

11. The system for delivering oxygen of claim 10, further comprising a status display system for indicating a status of the system.

12. The system for delivering oxygen of claim 11, wherein the display system is a plurality of light-emitting diode (LED) lights, wherein the display system is configured to operate the LED lights in a plurality of different modes corresponding to different statuses of the system.

13. An adaptive controller for delivering a small dosage amount of oxygen to a patient, said controller comprising:
    a non-invasive oximeter sensor system configured to measure blood hemoglobin saturation in the patient, said oximeter sensor system generating a plurality of blood hemoglobin saturation output signal values over a given period of time, sequentially representative of said blood hemoglobin saturation, the oximeter sensor, the oximeter sensor system including and operating in parallel: (1) a first oximeter coupled to an oro-nasal mask piece of an aircraft passenger breathing mask to contact a nose of the patient, the first oximeter configured to detect oxygen saturation of hemoglobin based on absorption of light of two different wavelengths; (2) a capnometer configured to measure carbon dioxide in gas expired by the patient; (3) a second, visible light spectroscopy (VLS) tissue oximeter configured to detect oxygen levels in microvascular tissues based on wavelengths shorter than the two different wavelengths used by the first oximeter, and (4) a second oximeter on a mask strap of the aircraft passenger breathing mask, the second sensor device configured to detect a second value of the blood oxygen saturation level of the user from a back of a neck of the user; and
    a processor configured to:
       generate and adjust a running average of said blood hemoglobin saturation output values;

generate an output signal that is a function of said running average;

identify possibly invalid output signal values in response to receiving the blood hemoglobin saturation output signal values to evaluate a plurality of said blood hemoglobin saturation output signal values;

based on said evaluation, provide a processed output signal; and substitute respective output signals for each of said possibly invalid output signal values thereby forming a sequence of valid output signals; and adjust a flow of oxygen to the patient using the running average.

14. The adaptive controller of claim 13 wherein the first oximeter is a pulse oximeter and said plurality of blood hemoglobin saturation output signal values are oxygen saturation of hemoglobin values as measured by the pulse oximeter.

15. The adaptive controller of claim 13 wherein the processor is further configured to:

identify the possibly invalid output signal values by providing a sequence of valid output signal values, exclusive of said identified possibly invalid output signal values; and generate a running average of said sequence of valid output signal values and for providing said running average as said processed output signal.

16. The adaptive controller of claim 15 wherein the processor is further configured to:

compare each of said plurality of output signal values to said running average to identify as possibly invalid any output signal value which differs from said running average by more than a predetermined amount.

17. An adaptive controller for delivering a fractional amount of oxygen to a patient, said controller comprising:

a sensor configured to be coupled to the patient and to measure blood oxygen level in the patient and for providing a plurality of output signal values, sequentially representative of said measured blood oxygen level, the sensor including and operating in parallel: (1) a first oximeter coupled to an oro-nasal mask piece, the first oximeter configured to be coupled to a nose of the patient and configured to detect oxygen saturation of hemoglobin based on absorption of light of two different wavelengths; (2) a capnometer configured to measure carbon dioxide in gas expired by the patient; (3) a second, visible light spectroscopy (VLS) tissue oximeter configured to detect oxygen levels in microvascular tissues based on wavelengths shorter than the two different wavelengths used by the first oximeter, and (4) a second oximeter on a mask strap of the aircraft passenger breathing mask, the second sensor device configured to detect a second value of the blood oxygen saturation level of the user from a back of a neck of the user;

a processor coupled to the sensor and configured to generate a running average of said plurality of output signal values and for subtracting said running average from a target value, representing a desired blood oxygen level for the patient, to produce a difference signal; and a feedback controller configured to receive said difference signal and adjust the fractional amount of oxygen to be delivered to the patient to minimize said difference signal in magnitude, wherein the fractional amount of oxygen delivered is adjusted in response to detecting erroneous signals.

18. A method for adaptively controlling the fractional amount of oxygen delivered to a patient comprising the steps of:

a) measuring the blood hemoglobin saturation in the patient during a plurality of intervals over a given period of time and providing said measured values as an output signal using a first oximeter sensor coupled to an oro-nasal mask piece and configured to contact a nose of the patient and a second oximeter sensor on a mask strap of the aircraft passenger breathing mask, the first oximeter sensor and the second oximeter sensor configured to detect oxygen saturation of hemoglobin based on absorption of light of two different wavelengths;

b) evaluating each of the measured values of said output signal to identify possibly invalid output signal values;

c) eliminating said identified possibly invalid output signal values from said output signal to produce a processed output signal;

d) adjusting the fractional amount of oxygen delivered to the patient in a sense to minimize any difference between said processed output signal and a predetermined desired blood hemoglobin saturation signal.

* * * * *